United States Patent [19]

Chan

[11] Patent Number: 4,973,168
[45] Date of Patent: Nov. 27, 1990

[54] VACUUM MIXING/BONE CEMENT CARTRIDGE AND KIT

[76] Inventor: Kwan-Ho Chan, 271 MacNab Street South, Hamilton, Ontario, Canada, L8P 3E2

[21] Appl. No.: 296,690
[22] Filed: Jan. 13, 1989
[51] Int. Cl.$^5$ .................. B01F 13/06; B01F 15/02
[52] U.S. Cl. .................. 366/139; 206/219; 366/130; 366/163; 366/255
[58] Field of Search ............... 366/139, 142, 144, 163, 366/183, 194, 255, 256, 243, 332, 333, 602, 130, 150; 222/152, 386, 391, 568, 327, 185, 325, 326; 206/219, 221, 570, 571, 572, 229, 438, 497, 524.8, 459, 627, 623, 631, 631.1; 141/18, 192, 329, 331, 332, 8, 199; 604/56, 87, 88, 200, 218, 232, 239, 241; 128/92 VQ

[56] References Cited

U.S. PATENT DOCUMENTS

| | | | |
|---|---|---|---|
| 1,718,603 | 6/1929 | Smith | 141/18 X |
| 1,744,449 | 1/1930 | Dawson | 366/333 |
| 1,819,258 | 8/1931 | Nevin | 604/200 |
| 2,453,914 | 11/1948 | Hollenback . | |
| 2,696,022 | 12/1954 | Steinbock et al. . | |
| 2,973,187 | 2/1961 | Wehmer . | |
| 3,131,912 | 5/1964 | Steinbock, Jr. . | |
| 3,164,303 | 1/1965 | Trautmann | 366/333 X |
| 3,343,817 | 9/1967 | Carangelo et al. . | |
| 3,358,971 | 12/1967 | Steinbock, Jr. . | |
| 3,559,961 | 2/1971 | Bergendal . | |
| 3,560,162 | 2/1971 | Mittleman | 366/256 X |
| 3,610,586 | 10/1971 | Price et al. . | |
| 3,640,510 | 2/1972 | Lea . | |
| 3,988,499 | 10/1976 | Reynolds | 206/497 X |
| 4,185,072 | 1/1980 | Puderbaugh et al. . | |
| 4,199,866 | 4/1980 | Drury . | |
| 4,277,184 | 7/1981 | Solomon . | |
| 4,338,925 | 7/1982 | Miller | 128/92 VQ |
| 4,463,875 | 8/1984 | Tepic . | |
| 4,551,135 | 11/1985 | Gorman et al. . | |
| 4,605,129 | 8/1986 | Detzel et al. | 206/219 X |
| 4,671,263 | 6/1987 | Draenert . | |
| 4,676,406 | 6/1987 | Frischmann et al. | 366/256 X |
| 4,721,390 | 1/1988 | Lidgren . | |
| 4,735,509 | 4/1988 | Rausch | 366/333 |
| 4,758,096 | 7/1988 | Gunnarsson | 366/139 |
| 4,799,801 | 1/1989 | Bruning | 366/255 |
| 4,808,184 | 2/1989 | Tepic . | |

FOREIGN PATENT DOCUMENTS

| | | |
|---|---|---|
| 0178658 | 4/1986 | European Pat. Off. . |
| 319921 | 3/1902 | France .................. 366/332 |
| WO84/03830 | 11/1984 | Japan . |
| WO86/06618 | 11/1986 | World Int. Prop. O. . |

OTHER PUBLICATIONS

MIT VAC ®, "Vacuum Mixing System", *MITAB* (article) ) (date unknown).
Zimmer ®, "Vacuum Mixing System", Z (article) (1986, month unknown).
DePuy Vacu-Mix ®, "Orthopedic Cement Mixing System" (4/1977).
Stryker ®, "Simple, Sterile, Disposable MixEvac" (8/1978).
Howmedica, "The Simplex Enhancement Vacuum Mixer", No. 2, *JBJS* 69-A, Feb. 1987.
Zimmer ®, "Cement Centrifugation System" (article) (1984, month unknown).

*Primary Examiner*—Harvey C. Hornsby
*Assistant Examiner*—Scott J. Haugland
*Attorney, Agent, or Firm*—Sherman and Shalloway

[57] ABSTRACT

A two-component bone cement mixing system comprises a cartridge mixer having an interior volume containing a first predetermined quantity of a solid bone cement component under vacuum pressure; an ampoule containing a second predetermined quantity of a liquid bone cement component; a fluid transfer element for fluidically connecting the cartridge mixer and the ampoule for transfer of the liquid bone cement component to the cartridge mixer; and a plug element, receivable within the ampoule, for automatically hermetically sealing the fluid transfer element against passage of a material therethrough upon completion of the transfer of the second predetermined quantity of the liquid bone cement component into the cartridge mixer. The two-component bone cement mixing system allows in vacuo mixing of liquid monomeric and solid polymeric bone cement components without air being incorporated into the mixture and insures the prevention of air passage into the cartridge mixer during and/or after monomer transfer.

37 Claims, 10 Drawing Sheets

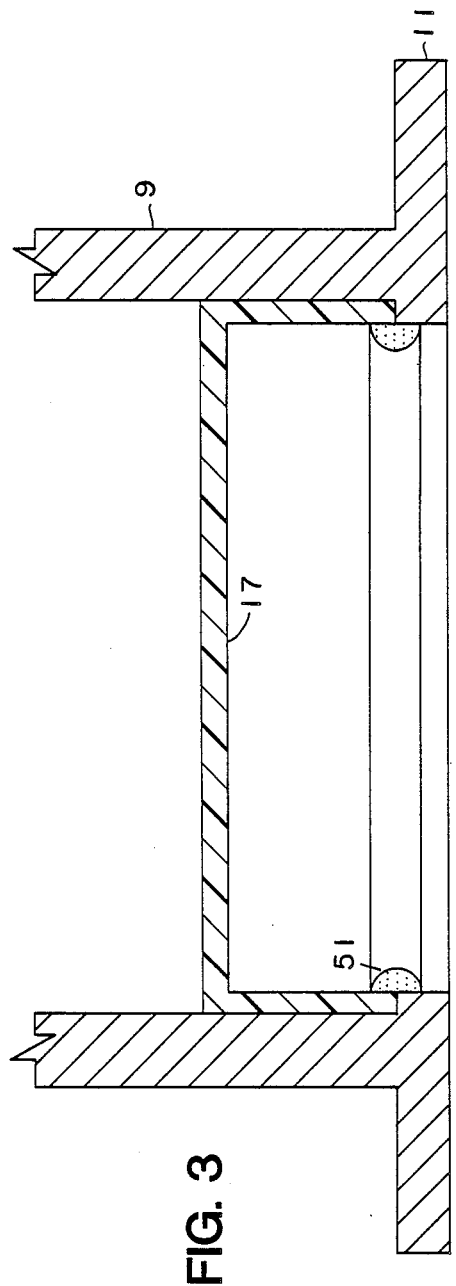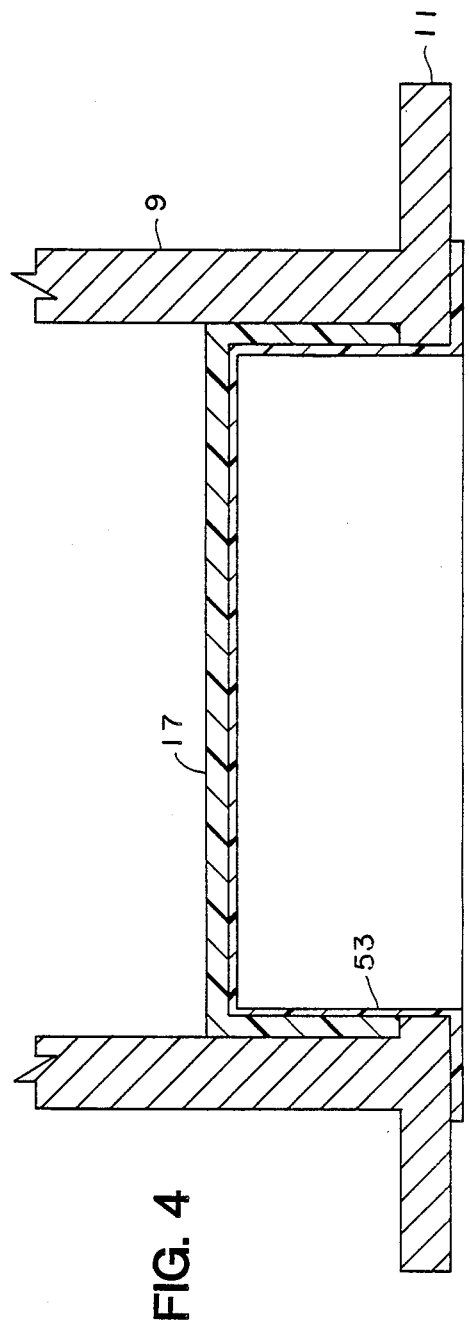

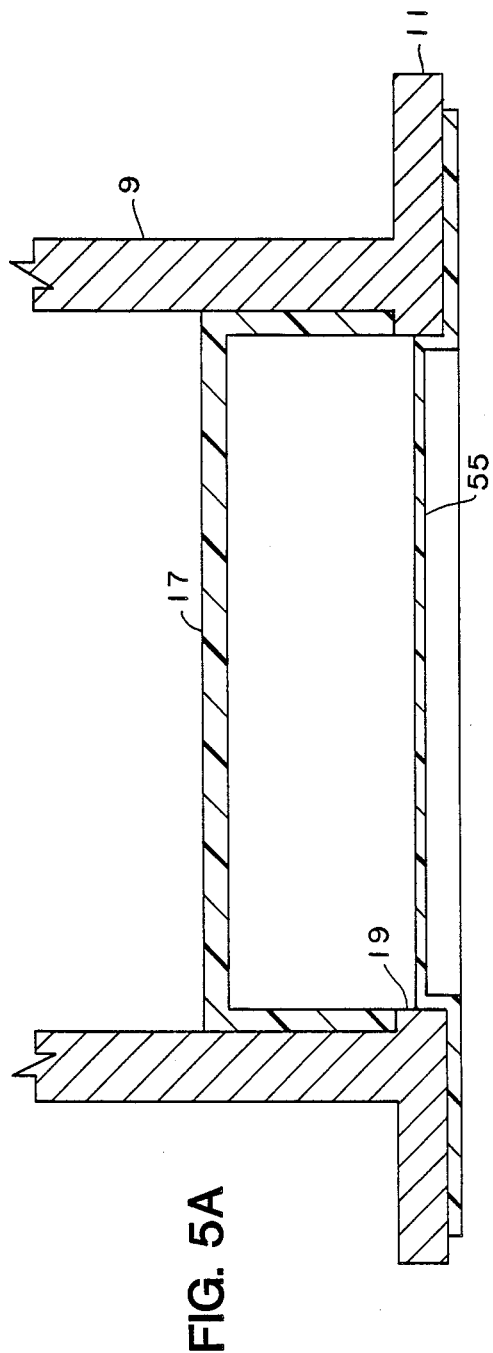
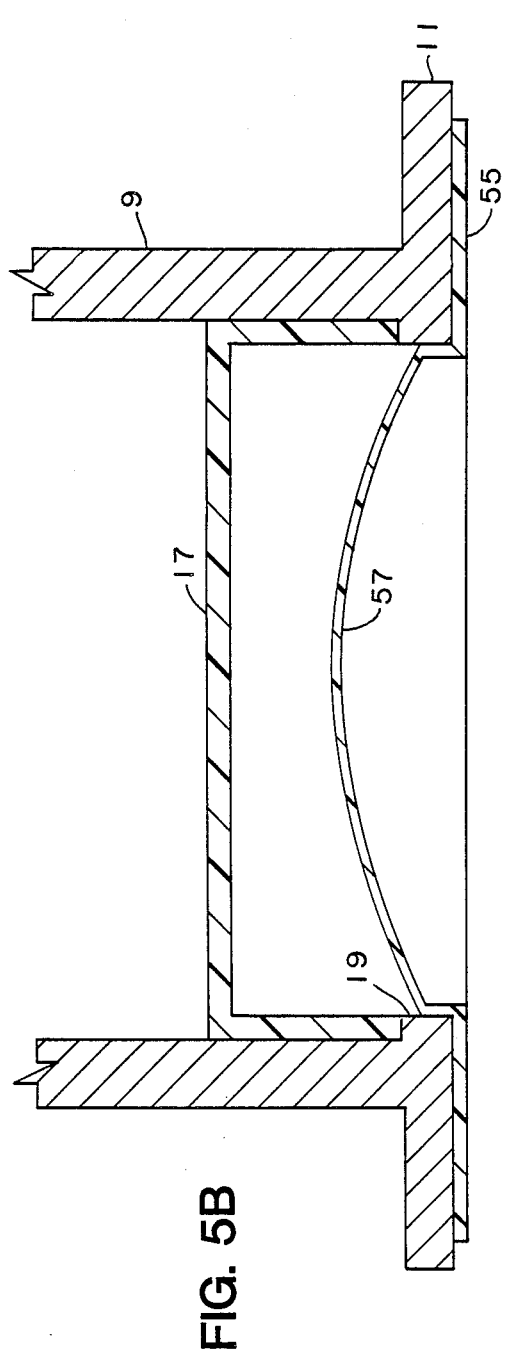
FIG. 5A
FIG. 5B

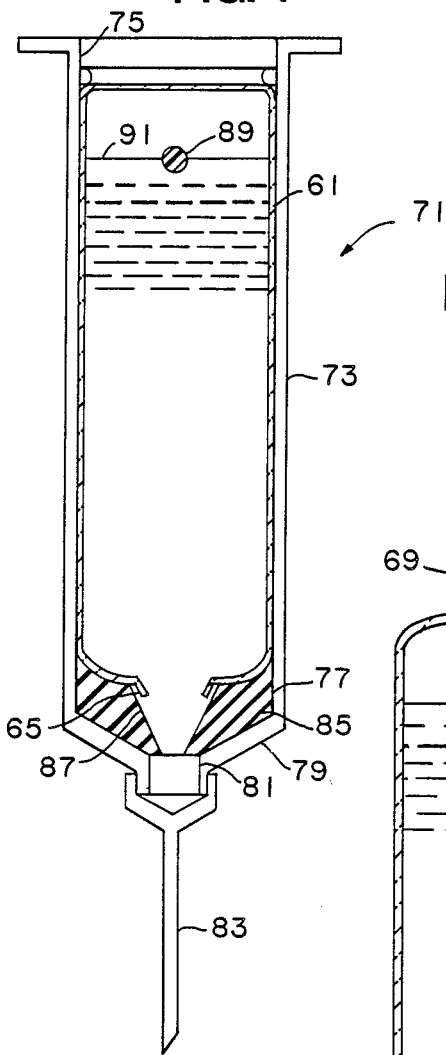
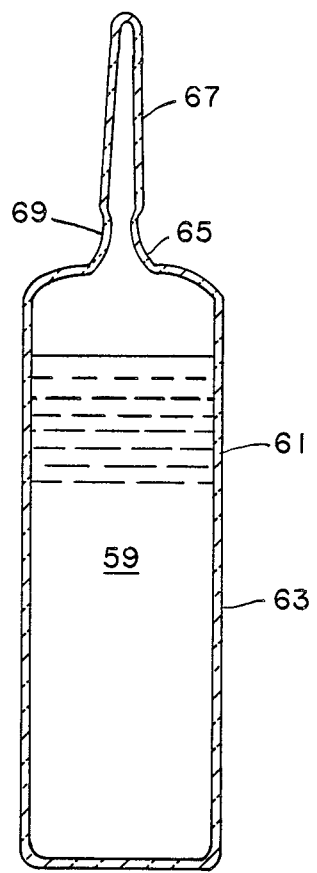
FIG. 7
FIG. 6

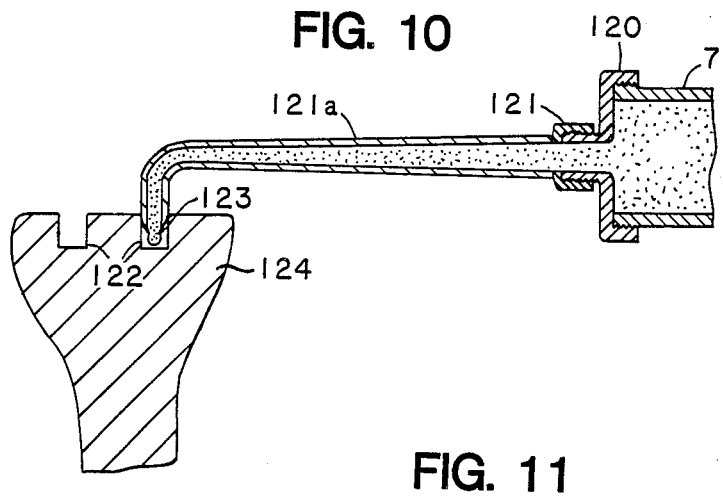
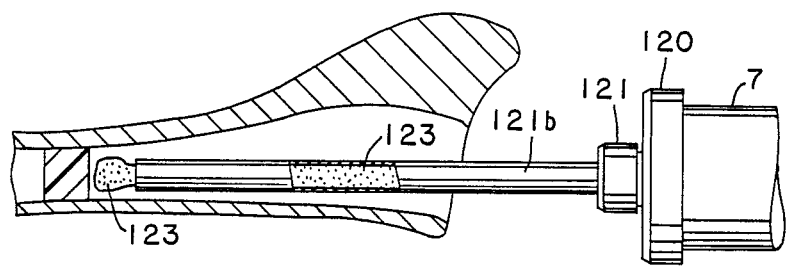
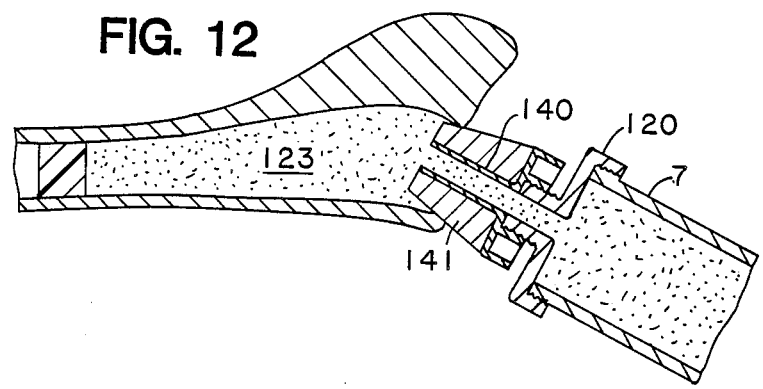

VACUUM MIXING/BONE CEMENT CARTRIDGE AND KIT

BACKGROUND OF THE INVENTION

1. Field of the Invention:

The present invention relates to the mixing of materials in the substantial absence of air. More particularly, the present invention relates to the preparation of a bone cement from a solid component and a liquid component by admixing the two components under vacuum pressure, an apparatus to effect such mixing and a kit to provide a surgeon with all the necessary materials to prepare a two-component bone cement substantially free of entrained air.

Additionally, the present invention relates to a method of preparing a bone cement from a solid component and a liquid component by admixing the two components under vacuum pressure, wherein such admixture takes place under a predetermined degree of chilling so as to control the rate of hardening of the cement, and subsequently pressurizing the admixture to inhibit entrainment of gaseous materials.

2. Description of the Prior Art:

In many orthopedic surgical procedures, it is necessary to employ a bonding material to set implants such as pins and artificial joints in bone. The cement which is employed for this purpose is generally a polymeric material which is prepared by copolymerization of its components as needed. Because of the necessity for a fairly quick setting material the cement is almost universally prepared by a surgical assistant during the course of the operation in the sterile field of the operating room. The preparation of the cement involves admixture of the cement components in a suitable reaction vessel to form a uniform polymeric reaction product. The cement is usually a (meth)acrylic material comprising a reaction product of a monomer and a polymer, e.g. methylmethacrylate monomer and polymethylmethacrylate or methylmethacrylate-styrene copolymer. In order to provide a cement which has the desired properties and which has the desired fixation of the implants, it is necessary that the compounds be uniformly and thoroughly mixed so that a homogeneous reaction product is produced. During the mixing and subsequent reaction, there are produced various vapors which may comprise a gaseous form of a volatile component or a gaseous reaction product. Because of the noxious (and toxic) nature of such vapors it is highly undesirable to be exposed to them, particularly for extended periods of time in the course of multiple preparations. Since it is necessary that the mixing be carried out for extended periods of time in order to ensure a uniform reaction product and a minimum concentration of volatile reactants, the period of exposure to harmful vapors can be substantial.

Nonetheless, despite the knowledge of the aforesaid difficulties, all known techniques for the mixing of bone cements have serious drawbacks, the most frequent being:

poor mixing, depending on the individual mixing technique;

high exotherm, due to considerable amounts of monomeric component necessary to produce a workable cement mass by conventional mixing techniques; and creation of porosities, by inclusion and entrapment of air bubbles as well as by evaporation of excess monomer resulting in the degradation of the mechanical properties of the cured cement.

In order to avoid these problems, various attempts to provide vacuum mixing devices have been made.

U.S. Pat. No. 4,185,072, to Puderbaugh et al., discloses an orthopedic cement mixer which comprises a mixing vessel within an evacuable housing and mixing vanes operable from outside of the housing. The housing is provided with vacuum conduits which can be connected to a vacuum source for withdrawing vapors and/or gaseous reaction products from within the housing.

U.S. Pat. No. 4,277,184, to Solomon, discloses a disposable orthopedic implement for mixing and dispensing bone cement comprising a chamber having a barrel portion and a neck portion; a member which is reciprocable within the barrel portion of the chamber; a mixing member operatively and axially receivable within the reciprocable member; and means for rotating the mixing member within the barrel portion of the chamber.

U.S. Pat. No. 4,463,875, to Tepic, discloses an apparatus for preparing and applying a two-component cement, wherein the components are vacuum packaged in elongated flexible fluid-tight compartments and those compartments are confined in abutting relation with a seal existing around the abutting portions of the compartments. In operation, one of the compartments is gradually collapsed to force its contents to break through the abutting wall portions into the other compartment while the extension of the other compartment is controlled as it receives the contents of the one compartment. Then the other compartment is gradually collapsed to force its contents into the one compartment while controlling the extension of the one compartment. The two compartments are alternately collapsed and controlledly extended until the components therein form a homogeneous cementitious mixture. A nozzle is then attached to one of the compartments in lieu of the other compartment and the one compartment is collapsed to expel the mixture through the nozzle.

Published International patent application WO 84/03830, to Himeno, discloses an apparatus for mixing a bone cement wherein the solid component of a bone cement is sealed in a flexible bag along with a sterilizing gas. The gas is then withdrawn through a hypodermic needle to evacuate the gases within the bag. The liquid component of the bone cement is then injected into the bag, and the bag kneaded to mix the cement. After kneading the bag may be opened to remove the ready-to-use cement.

U.S. Pat. No. 4,551,135, to Gorman et al., discloses a syringe for extrusion of a semi-plastic mass. The syringe is designed so as to permit the mixing of two components of a plasticizable mixture within the syringe barrel, i.e. a liquid component may be injected into the syringe barrel containing particulate solids while venting air therefrom or a liquid component may be drawn into the syringe barrel which is only partially filled with particulate solids.

European Published patent application No. 0 178 658 (and U.S. Pat. No. 4,721,390), to Lidgren, disclose a method for producing bone cement for fixing prostheses. In order to prevent large amounts of air from being stirred into the mixture, mixing of the bone cement components occurs under vacuum. Preferably the bone cement components are mixed in a feed device from which the mixture may be pressed out, and to effect this aspect of the invention there are provided an agitator which is connectable to the feed device and a vacuum source which is also connectable to the feed device.

Published International patent application WO 86/06618, to Tepic, discloses a method of preparing a two component cement wherein the evacuated interspaces between powder component particles are flooded with liquid component, followed by mechanical homogenization of the resulting mass. The method is preferably performed in a syringe-type container whereby the liquid component in an ampoule is injected through the piston member of the syringe, and the syringe is fitted with an axially collapsible mixing element, so as to not interfere with movement of the piston for extrusion of the cement from the syringe.

U.S. Pat. No. 4,671,263, to Draenert, discloses a device for applying bone cement wherein the bone cement, prior to its application, is prepressurized at an adjustable pressure and then applied at a controllable pressure. The prepressurization suppresses bubble formation in the bone cement and the controllable pressure aids desired stratification of the bone cement around the prosthesis during application.

The brochures "MIT VAC® Vacuum Mixing System" and "ZIMMER® Vacuum Mixing System" (Copyright 1986) both disclose a bone cement mixing system providing a vacuum pump and either an evacuable mixing bowl; or an evacuable housing (with mixer), for mixing in a cartridge for a bone cement gun.

The brochure "DePuy Vacu-Mix® Orthopedic Cement Mixing System"(April 1977) discloses an open housing, for a mixing bowl, which may be connected to a vacuum pump so as to draw off vapors from above the mixing bowl.

The brochure "Stryker® Mix Evac®" (copyright August 1978) discloses a disposable enclosed housing which comprises a mixing vessel within a housing, a cover for the housing and a mixing element operable through the cover. The housing may be connected to a vacuum supply to draw air through the cover and out through the housing thus preventing monomer vapors from being released to the operating room atmosphere.

The advertisement "The Simplex Enhancement Vacuum Mixer", JBJS, No. 2, 69-A, February 1987, discloses an evacuable housing, having a cover equipped with an externally operable mixing element, which will hold a bone cement gun cartridge for mixing of bone cement in the cartridge. The housing may be connected to a vacuum source to allow mixing under vacuum pressure.

The brochure "ZIMMER® Cement Centrifugation System"(Copyright 1984) discloses a system wherein after mixing of the bone cement, the bone cement is placed in a cartridge for a bone cement gun and centrifuged to help decrease cement porosity.

Numerous other devices have been conceived for the conduct of mixing operations under a controlled atmosphere or under vacuum. Illustrative of such devices are U.S. Pat. No. 2,453,914, to Hollenback, which discloses a device for mixing plaster compounds comprising a bowl, a cover for said bowl which carries an externally operated mixer for the agitation of the bowl contents and an orifice for attachment to a vacuum source to de-aerate the bowl contents.

U.S. Pat. No. 2,696,022, to Steinbock et al., discloses an investment mixer comprising a mixer bowl, a cover therefor, an agitator extending through the cover, and a fitting on the cover for connection to a vacuum source.

U.S. Pat. No. 2,973,187, to Wehmer, discloses a vacuum spatulator comprising a mixer bowl, a cover therefor, an agitator extending through the cover, and a fitting whereby the covered bowl may be placed under vacuum.

U.S. Pat. No. 3,131,912, to Steinbock, Jr., discloses an investment mixer comprising a mixing bowl, a cover for the mixing bowl, an externally operated agitator extending through the mixing bowl, and a fitting on the cover allowing evacuation of the atmosphere in the mixing bowl by connection to a vacuum source.

U.S. Pat. No. 3,343,817, to Carangelo et al., discloses an apparatus for mixing materials in the absence of air comprising a mixing bowl having an externally operated agitator in the bottom thereof and a piston receivable within the mixing bowl. The piston has an aperture therein so that, when it is lowered into place on materials to be mixed in the bowl, air caught below the piston is expelled. When the piston contacts the surface of materials to be mixed, the aperture is closed and agitation initiated.

U.S. Pat. No. 3,358,971, to Steinbock, Jr., discloses an investment mixer comprising a mixer bowl, a cover therefor, an agitator extending through said cover into said mixing bowl and an aperture for removing gases within the mixing bowl by connection to a vacuum pressure supply.

U.S. Pat. No. 3,559,961, to Bergendal, discloses an apparatus for the preparation of dental amalgams comprising a container of two halves, one of which is fitted with an outlet connectable to a vacuum pressure supply. Components to be formed into an amalgam are placed within the container, the container atmosphere is evacuated, and the evacuated container is then agitated to mix the contents thereof.

U.S. Pat. No. 3,610,586, to Price et al., discloses a dental mixing system in which prepackaged ingredients to be mixed for dental applications are stored within a container which maintains the ingredients isolated from each other prior to usage. The ingredients are intermixed by placing the container in a mixing device which rotates the base of the container while maintaining the cover stationary. A knife portion integral with the container bottom severs an isolating membrane stretched over a portion of the cover, during operation of the mixer, and permits the ingredients to mix. Through rotation of the container bottom, a homogeneous mixture is realized with a mixing paddle integral with the stationary container top or cover.

U.S. Pat. No. 3,640,510, to Lea, discloses a vacuum mixing system for dental materials comprising a closed container, an externally operated rotary stirring device therein and means for applying vacuum pressure to the contents of the closed container.

U.S. Pat. No. 4,199,866, to Drury, discloses a dental amalgamator which prevents mercury vapor, given off during amalgamation, from polluting the air in the neighborhood of the amalgamator. The amalgamator comprises a casing carrying a capsule holder and a drive means for the holder, a lid movable to a closed position in which it cooperates with the casing to form an enclosure for a capsule held by the holder, the enclosure having air inlets allowing air to flow from the atmosphere into the enclosure. A vacuum pump is arranged to communicate with the enclosure via a mercury filter medium, so that during amalgamation air is drawn into the enclosure, over the capsule, and then through the mercury filter where mercury vapors are removed.

Nonetheless, a need continues to exist for a simple two-component bone cement mixing system, which will allow mixing under vacuum but which will require little in the way of equipment. Moreover, a need also exists for a vacuum mixing system which can be readily manipulated without fear of premature loss of vacuum.

SUMMARY OF THE INVENTION

In a first embodiment, the present invention provides a two-component bone cement mixing system comprising:

(A) a cartridge mixer means, having an interior volume containing a first predetermined quantity of a solid bone cement component under vacuum pressure, for mixing said first predetermined quantity of a solid bone cement component with a second predetermined quantity of a liquid bone cement component in the substantial absence of air to form a third predetermined quantity of a fluid two-component bone cement;

(B) container means, containing said second predetermined quantity of a liquid bone cement component, for holding a liquid bone cement component;

(C) fluid transfer means, operably connectable to said cartridge mixer means and said container means, for fluidically connecting said container means and said cartridge mixer means to transfer said second predetermined quantity of a liquid bone cement component from said container means to said cartridge mixer means;

(D) plug means, receivable within said container means, for automatically hermetically sealing said fluid transfer means against passage of a material therethrough upon completion of the transfer of said second predetermined quantity of a liquid bone cement component from said container means to said cartridge mixer means therethrough.

In a second embodiment, the present invention provides a cartridge mixer, having an interior volume, useful for the mixing of a first predetermined quantity of a solid bone cement component with a second predetermined quantity of a liquid bone cement component to form a third predetermined quantity of a fluid two-component bone cement, said cartridge mixer comprising cartridge means, receivable within a bone cement gun, for containing said third predetermined quantity of a fluid two-component bone cement, said cartridge means including piston means, operatively engageable by said bone cement gun and moveable within said cartridge means, for dispensing of said fluid two-component bone cement from said cartridge means;

mixer means, detachably connected to said cartridge means, for agitating the contents of said cartridge means, said mixer means including inlet port means for passage of a second predetermined quantity of a liquid bone cement component into said cartridge mixer;

hermetic sealing means for sealing said connected cartridge means and mixer means against the ingress of air.

In a third embodiment, the present invention provides a two-component bone cement kit comprising:

(A) a vacuum packed cartridge mixer, defining an interior volume, containing a first predetermined quantity of a powdery bone cement component, said cartridge mixer comprising:

a cartridge member, receivable within a bone cement gun, comprising a hollow, air-impermeable cartridge body member having a longitudinal axis, and a first open end and a second open end spaced apart on said longitudinal axis, an air-permeable piston member, axially slidable within said hollow cartridge body, disposed within said cartridge body, proximate said first end of said cartridge body, to close said first end of said cartridge body, releasable hermetic sealing means for releasably hermetically sealing said piston member to said cartridge body proximate said first end of said cartridge body, a mixer member comprising a hollow, air-impermeable mixer body having a longitudinal axis, and a first open end and a second open end spaced apart on said longitudinal axis, releasable connection means for releasably coaxially hermetically sealingly connecting said second end of said cartridge body member to said second end of said mixer body for fluidic communication between said cartridge body member and said mixer body, and cap means for hermetically sealing said first end of said mixer body, said cap means including self-sealing aperture means, pierceable by a hollow needle, for fluidic communication with said interior volume of said cartridge mixer through said hollow needle when pierced by said hollow needle and hermetically sealed closure of said interior volume when said hollow needle is withdrawn, and mixing means for agitating a material contained within said interior volume of said cartridge mixer;

(B) an ampoule, defining an interior volume, containing a second predetermined quantity of a liquid bone cement component, said ampoule comprising a liquid bone cement component impermeable body member having a longitudinal axis, spout means, having a predetermined diameter, for fluidic communication with said interior volume of said ampoule and removable closure means for hermetically sealing said spout means;

(C) an injector comprising a hollow injector body member having a longitudinal axis and a first open end and a second open end spaced apart on said longitudinal axis, said hollow injector body member slidingly, coaxially receivable of said ampoule, a cap member, disposed on said second open end of said hollow injector body for closure thereof, said cap member including a fluid conduit, coaxial with said hollow injector body, for passage of a fluid through said cap member, hollow needle means, pierceable of said self-sealing aperture means, hermetically connectable to said fluid conduit, for passage of fluid into said interior volume of said cartridge mixer, resilient support means, hermetically sealingly connecting said second end of said hollow injector body and said cap member, for engagingly contacting said ampoule, said resilient support means including a fluid passage tapering toward and fluidically connected to said fluid conduit, said fluid passage coaxial with said hollow injector body and receivable of said ampoule spout means; and (D) float means, having a specific gravity less than said liquid bone cement component, for hermetically sealingly closing said fluid passage in said resilient support means.

BRIEF DESCRIPTION OF THE DRAWING FIGURES

FIG. 3 is a schematic, partially sectioned, illustration of a first embodiment of a releasable hermetic closure for a piston of a bone cement cartridge.

FIG. 4 is a schematic, partially sectioned, illustration of a second embodiment of a releasable hermetic closure of a piston of a bone cement cartridge.

FIGS. 5A and 5B are schematic, partially sectioned, illustrations of a third embodiment of a releasable hermetic closure of a piston of a bone cement cartridge.

FIG. 6 is an illustration of a container for liquid bone cement component.

FIG. 7 is a schematic, partially sectioned, illustration of a liquid bone cement injector according to the presently claimed invention.

FIG. 10 is a sectional view of the application of bone cement to a bone cavity in a bone.

FIG. 11 is a view partially in section illustrating the deposition of bone cement into the femoral canal.

FIG. 12 is a sectional view illustrating pressurization of bone cement in the federal canal.

DETAILED DESCRIPTION OF THE INVENTION

It is common practice, in joint surgery today, to anchor components of replacement joints by using a bone cement comprising a two-component resin which polymerizes during the operation at normal temperatures and which, on account of its properties, leads to an interlocking of the prosthesis component in the bony sheath. Because of its physical properties, the bone cement shrinks onto the prosthesis resulting in a closed metal-to-cement contact.

The bone cements commonly used are polymethylmethacrylate consisting of powdery bead polymers which are superficially dissolved by liquid monomers and embedded during the polymerization process. During mixing, the polymer is immersed in the monomers. The polymethylmethacrylate beads are superficially dissolved and embedded in a composite manner. Such a composite structure can be compared with concrete, where air bubbles are likewise included during mixing. Moreover, when the monomer immerses the polymer beads, filling defects remain. These defects are termed "lee phenomena". Furthermore, in the case of bone cements, the monomer liquid evaporates during the exothermic polymerization, whereby further bubbles are formed. The bubbles formed as mentioned above constitute the major portion of the gas enclosures in bone cements.

The chemical reaction of the above-mentioned bone cements is initiated by a starter reaction, wherein, typically, dibenzoyl peroxide is activated by an activator such as p-aminotoluidine and then the radical chain polymerization is started. This polymerization proceeds exothermically. The monomer itself is stabilized by hydroquinone. Some bone cements are further stabilized by chlorophyll with simultaneous coloring. The storability of the monomer liquid can also be stabilized by vitamin C.

In the processing phase, following the mixing phase, the bone cement is applied to the femoral medullary canal or to the bony acetabulum which are both prepared to anchor the cemented prosthesis components; the application of the bone cement is normally performed by hand and sometimes using a syringe.

Using a syringe, the cement anchorage in the bone can be markedly improved. Therefore, so-called "bone cement guns" have been proposed, the principal of which is to impact the cement in the plugged medullary canal to provide transverse anchorage. With bone cement guns, the filling of the bone bedding is performed in different ways. On the one hand, filling is done from above in the downward direction or, on the other hand, it is also performed in the other direction, i.e. upwardly from below, by means of a long nozzle.

With the aforementioned techniques in mind, the present invention provides a two-component bone cement mixing system which allows preparation of the two-component bone cement under vacuum pressure, whereby gaseous inclusions are minimized, and further allows the preparation of the bone cement in a cartridge which may then be directly loaded into a bone cement gun for immediate operative use.

Figure 1:
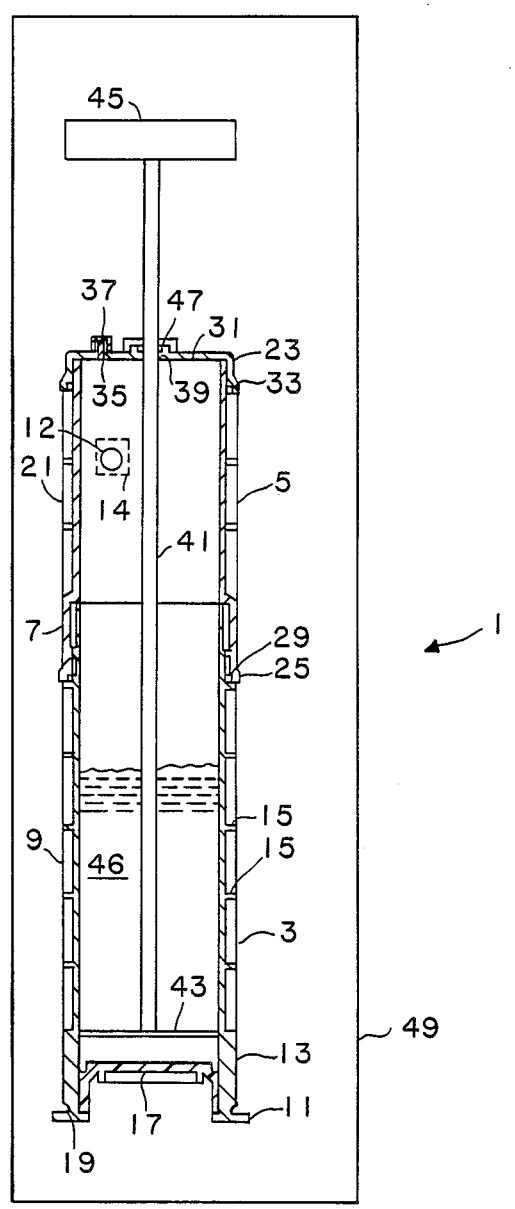
FIG. 1 is a schematic, partially sectioned, illustration of a double vacuum-packed cartridge mixer according to the present invention.
Figure 2:
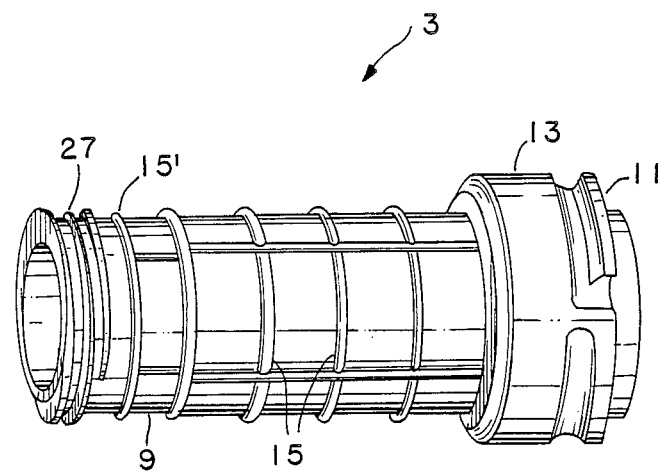
FIG. 2 is an isometric view of a bone cement cartridge according to the present invention.
Figure 8:
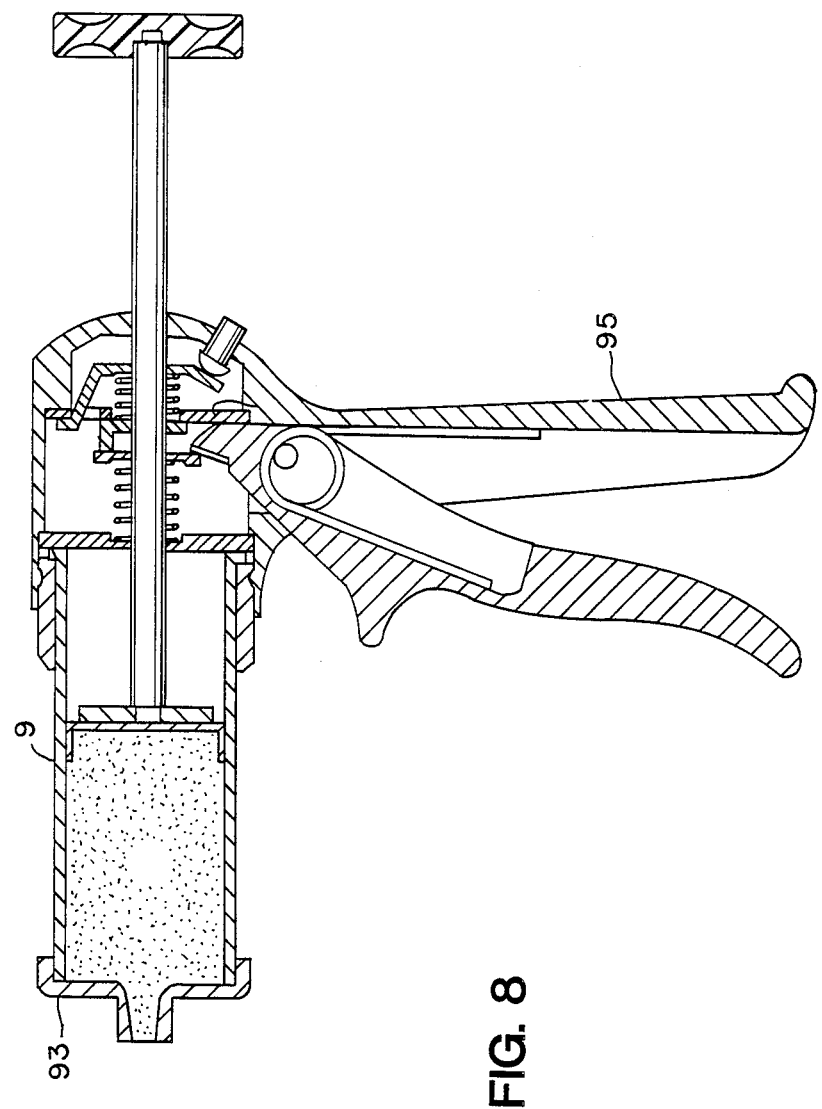
FIG. 8 is a sectional view of a bone cement gun containing a bone cement cartridge.

Turning now to FIG. 1 of the drawing, there is generally indicated at 1 a double vacuum-packed cartridge mixer according to the present invention. The cartridge mixer comprises a cartridge member 3 and a mixer member 5 which are detachably connected to each other. The cartridge member 3, as best seen in FIG. 2, comprises a hollow, air-impermeable cartridge body member 9 having a flange 11 at one end thereof along with a collar 13 whereby the cartridge body member may be mounted in a bone cement gun, as best seen in FIG. 8. The wall of the cartridge body member 9 may be reinforced with ribs 15 for added strength.

An air-impermeable piston member 17 is disposed within the cartridge body 9 proximate a first end 19 thereof so as to close the first end of the cartridge body member 9. The piston member 17 is axially slidable within the hollow cartridge body 9.

Figure 13:
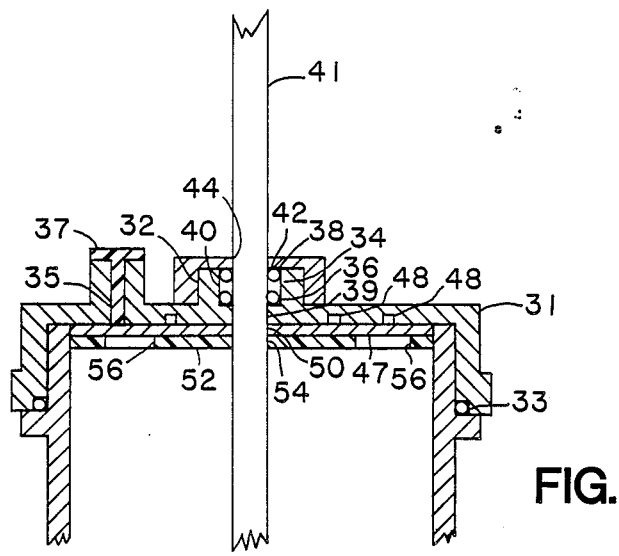
FIG. 13 is a detailed view of the capped end of the mixer body.
Figure 14:
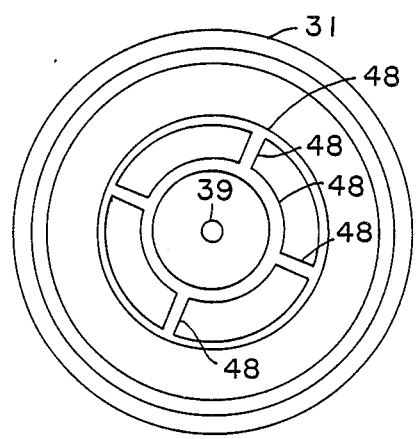
FIG. 14 is a plan view of the underside of the cap fixed on the first open end of the mixer body.
Figure 15:
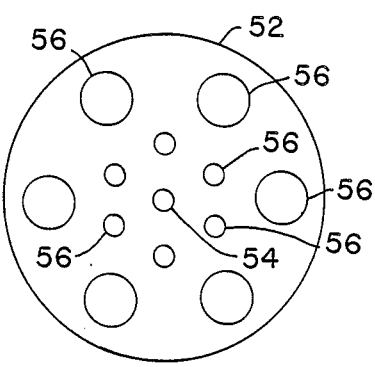
FIG. 15 is a plan view of a protective disc mounted on the underside of the cap fixed to the first open end of the mixer body.
Figure 16:
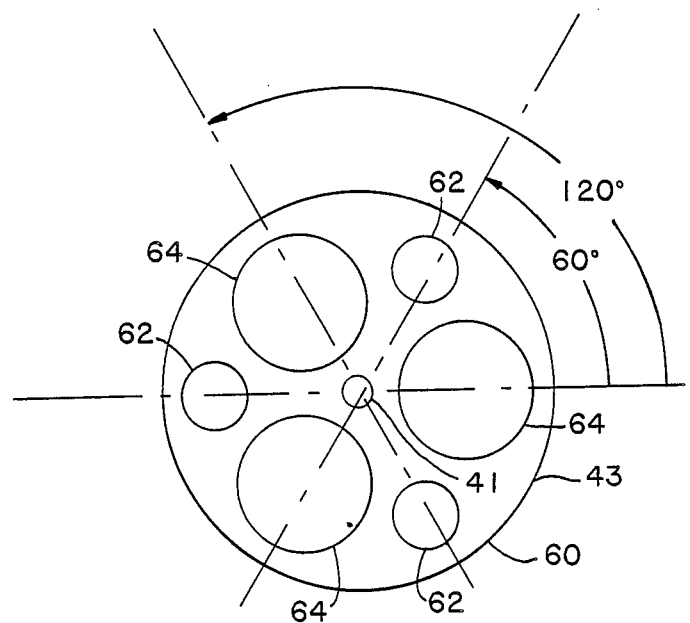
FIG. 16 is a plan view of the mixing element according to the present invention.

The mixer member 5 comprises a hollow, air-impermeable mixer body 21 having a first open end 23 and a second open end 25. The second open end 25 of the mixer body member 21 is provided with an internal screwthread (not shown) which is threadingly engageable of a screwthread 27 formed on the exterior of the second open end 7 of cartridge body member 9. By providing an O-ring 29 abutting the reinforing rib 15' a releasable coaxial hermetic seal of the cartridge body member to the mixer body member may be obtained when the cartridge body member and the mixer body member are threadingly engaged with one another. Of course, any other form of detachable connection capable of forming a hermetic seal may also be utilized, e.g., a snap-fit with O-ring sealing element. In a similar mannner, the cap 31 in combination with an O-ring 33 hermetically seals the first end 23 of the mixer body member 21. The cap 31 includes an aperture 35 which is closed by a self-sealing element 37 such as a rubber septum. The cap 31 is also provided with an additional aperture 39 through which the shaft 41 of a mixing element 43 passes. The shaft 41 is axially moveable in the aperture 39 and may also be rotated within the aperture 39. As may best be seen in FIG. 13, the aperture 39 is surrounded by an upstanding, circumferential wall 32 which forms a chamber 34 receivable of a plurality of alternating O-rings and washers (two O-rings 36 and 38 and one washer 40 being illustrated). The chamber 34 is closed by a cap member 42 which is threadingly engageable with the outer circumference of wall 32, the cap member 42 having an perture 44 therein to allow passage of shaft 41 therethrough. The use of multiple O-rings alternating with washers (to form a packing box) is necessary in order to allow for reciprocal movement of shaft 41 while maintaining vacuum pressure within the mixer. The underside of the cap 31 (as best seen in FIG. 14) has a number of interconnected grooves 48 formed therein, with at least one of the grooves communicating with aperture 35. A porous membrane 47, e.g., a filter paper, is disposed over the underside of cap 31 so as to cover the grooves 48. The porous membrane 47 has an aperture 50 formed therein so as to permit passage of shaft 41 therethrough. The porous membrane 47 is in turn covered by a protective disc 52 (as best seen in FIG. 15). The protective disc 52 has a central aperture 54 to permit passage of shaft 41 therethrough. The protective disc 52 is additionally provided with a plurality of apertures 56 (which may vary in size, shape and pattern). The protective disc 52 protects the porous membrane 47 from being torn by mixing element 43. The function of the grooves 48, the porous membrane 47 and the protective disc 52 will be explained hereinbelow. As best seen in FIG. 16, the mixing element 43 comprises a plate 60 disposed substantially perpendicular to the shaft 41 and conforming substantially to the internal cross section of the cartridge body member and the mixer body member. The mixing element 43 has a number of holes 62, 64 formed therein so as to allow the mixer element to be reciprocated back and forth through a body of polymeric material 46 contained within the cartridge body member 9. The shaft 41 is provided with a manually graspable handle 45 so as to facilitate manipulation of the mixing element 43. In a preferred embodiment, the holes 62, 64 are circular in shape and disposed symmetrically about the plate 60 relative to the shaft 41 (which is concentric with the plate 60). The plate 60 is also circular in shape, and pairs of holes (one larger 64 and one smaller 62) are disposed on diameters of the plate and opposite one another relative to the center of the plate. Most preferably, three pairs of holes are used disposed on diameters of the plate which are offset 60° of arc from the adjacent diameters upon which holes are disposed; and each large hole 64 is immediately adjacent to two small holes 62 on the immediately adjacent diameters upon which holes are disposed. The centers of the smaller holes 62 all fall on the circumference of a first circle concentric with the plate 60; and the centers of the large holes 64 all fall on the circumference of a second circle concentric with the plate 60. Preferably, the diameter of the first circle is larger than the diameter of the second circle.

In use, the cartridge member 3 is loaded with a predetermined amount of a powdery polymeric component 46 and the mixer member 5 is then screwed onto the cartridge member so as to form a closed container. A hypodermic needle connected to a source of vacuum pressure is then inserted through the rubber septum 37 in aperture 35 and a vacuum is drawn within the cartridge mixer. Care must be taken so that the tip of the needle may enter the groove 48 but does pierce the porous membrane 47. This is because the powdery polymeric material would otherwise be sucked up through the needle and block further evacuation of air. The grooves 48, accordingly, allow a uniform application of vacuum across the cross-section of the mixer, while the porous membrane 47 prevents powdery polymeric material from being withdrawn from the mixer along with the air. The protective disc 52, in turn, prevents the mixer element 43 from damaging the porous membrane during handling prior to evacuation. Typically, a vacuum pressure of 30 millimeters of mercury or less is drawn in the cartridge mixer. The vacuum packed cartridge mixer is then vacuum packed within a container 49, such as an air-impermeable plastic bag. This double vacuum packing helps to assure a long and stable shelf life.

In order to provide a hermetic seal of the cartridge mixer, it is necessary that the piston member 17 be hermetically sealed also. However, the piston member 17 must also be axially slidable within the cartridge body member 9 so as to be capable of forcing the fluid bone cement from the cartridge member when the cartridge member is mounted in a bone cement gun. In other words, the piston member is not fitted within the cartridge member in an air tight manner, but rather just sufficiently tight to prevent leakage of the viscous cement mixture thereby. Accordingly, a releasable hermetic seal is necessary for the piston member. In this regard, FIG. 3 illustrates one embodiment of a releasable hermetic seal for the piston member 17 wherein a bead 51 of adhesive seals the piston in place. When the piston is engaged by the plunger of a bone cement gun, the bone cement gun plunger develops sufficient force to break the bead and allow movement of the piston through the cartridge body member 9. In a second embodiment, illustrated in FIG. 4, a thin layer of a resinous material 53 (e.g., polyethylene) is disposed over the piston member 17. In a manner similar to that of embodiment FIG. 3, the thin layer resinous material 53 may be broken by actuation of the plunger of a bone cement gun.

In a further embodiment, illustrated in FIGS. 5A and 5B, a thin diaphragm layer 55, e.g. of polyethylene, which is air-impermeable, is disposed across the first end 19 of cartridge body member 9 as shown in FIG. 5A to form the hermetic seal. When a vacuum is drawn in the interior of the cartridge mixer, the diaphragm layer 55 is bowed at 57 as shown in FIG. 5B. This embodiment not only provides a releasable hermetic seal, which may once again be broken by the actuation of the plunger of a bone cement gun, but also provides an indicator as to the maintenance of vacuum pressure within the cartridge mixer. In this regard, if the diaphragm layer 55 is bowed as shown in FIG. 5B, then this is a clear indication that vacuum pressure has been maintained within the cartridge mixer. If, however, after standing for long periods of time, a user finds the diaphragm layer 55 in the position illustrated in FIG. 5A, then this is a clear warning that vacuum pressure has been lost.

The liquid bone cement component 59 is preferably contained within a glass ampoule 61 due to the noxious and toxic nature of the liquid bone cement component, i.e. a (meth)acrylate monomer. The glass ampoule 61 comprises a body member 63 having a spout 65 and a removable closure 67 which may be broken off at the weakened neck 69 of the ampoule when desired.

An injector 71, as illustrated in FIG. 7, is utilized to transfer monomer to the interior of the cartridge mixer. The injector comprises a hollow injector body member 73 having a first open end 75 and a second open end 77. The injector body member 73 is coaxially receivable of the ampoule 61.

A cap 79 is disposed over the second open end 77 of the injector body 73 for closure thereof. The cap member 79 includes a fluid conduit 81, coaxial with the hollow injector body member 73, for passage of a fluid through the cap member. A hollow needle 83 is hermetically connectable to the fluid conduit 81 so as to allow a fluid medium to pass from the conduit 81 through the hollow needle. A resilient support 85, e.g., of silicone rubber, hermetically, sealingly connects the second end of the hollow injector body and the cap member. Additionally, the resilient support is provided with a fluid passage tapering toward and fluidically connected to the fluid conduit 81 in the cap member 79. When the opened ampoule 61 is inserted into the hollow injector body member 73, and the assembly then inverted to the position of FIG. 7 the resilient support 85 supports the ampoule and the spout portion 65 of the ampoule is received within the fluid passage 87.

It should be noted that temperature control is an important part of the mixing process. For the "dough" type cements in current use, such as Simplex ® and Zimmer-Regular ®, it has now been found that chilling the mixing container and the cement components aids in the prevention of excessively fast curing. In particular, when mixing cements under a vacuum pressure of 30 mm Hg or less, it has now been found desirable to chill the mixer and the cement components (powder and liquid) to a temperature below room temperature (20° C.), preferably less than 15° C., most preferably to about 12° C. ($\pm$2° C.), prior to bringing the solid and liquid components together in the mixer. This chilling is believed to be necessary due to the fact that, under vacuum pressures of 30 mm Hg or less, oxygen, which normally interacts with monomer free radicals to slow the polymerization of the monomer, is in short supply and will not effectively inhibit the polymerization reaction. In this regard, a thermometer or a temperature indicating strip, e.g., of the liquid crystal type, could be packaged with the mixer so as to allow the user to ascertain whether the mixer and its contents have been sufficiently chilled prior to use.

Prior to insertion of the opened ampoule 61 into the injector body member 73, a polyethylene ball 89 is placed in the ampoule, the polyethylene ball having a specific gravity less than the monomeric material and thus floating on the surface of the monomeric material. When the injector 71 is inverted so as to insert the needle 83 through the rubber septum 37 of the cartridge mixer, so as to inject monomeric material into the vacuum packed polymeric material contained therein, the polyethylene ball 89 will float on the surface of the monomer as illustrated in FIG. 7. As the monomer is drained from the ampoule 61 through fluid passage 87, fluid conduit 81 and hollow needle 83 into the cartridge mixer, by the vacuum pressure maintained in the cartridge mixer, the polyethylene ball will drop downward with the surface 91 of the liquid monomeric material. When the monomeric material is drained from the ampoule the polyethylene ball 89 will then hermetically seal the fluid passage 87 formed in the resilient support 85. This will prevent any air being drawn into the cartridge mixer around the edge of the ampoule 61 and between the ampoule 61 and the hollow body member 73. Thus, personnel transferring monomer to the polymeric material in the cartridge mixer are not required to closely monitor the progress of such transfer as they are with conventional syringe techniques or conventional stop cocks. In other words, when the contents of the ampoule are emptied, the fluid passage 87 is automatically sealed by the polyethylene ball 89 acting as a floating plug. Once transfer of the monomer has been completed, the needle 83 may be withdrawn from septum 37, and mixing of the two-component bone cement may then be conducted within the cartridge mixer. When the hollow needle is withdrawn from the cartridge mixer, air rushing through the hollow needle 83 will violently disengage the polyethylene ball 89 from the fluid passageway 87 in resilient support 85. This violent disengagement will cause the polyethylene ball 89 to bounce around within the empty ampoule 61. The noise so-produced is a further indication that a successful transfer of monomer into the cartridge mixer has been carried out without leakage of air into the cartridge mixer.

Mixing is readily effected by merely causing reciprocating motion of the mixing element 43 axially within the cartridge mixer. Mixing may be further facilitated by some rotation of the handle 45 during the reciprocating motion of the mixing element 43.

After mixing is completed, rubber septum 37 may then be pierced with a hollow needle so as to release the vacuum pressure within the cartridge mixer. Alternatively, the mixer member 5 may be provided with a vent hole 12 (shown as formed in the mixer body 21, but also could be provided in the cap 31) hermetically sealed with a pressure-sensitive adhesive tape 14; and it would only be necessary to peel away the tape to open vent hole 12 and release the vacuum. The mixer member 5 may then be detached from the cartridge member 3 and a suitable cap 93, as best seen in FIG. 8, may be placed over the second open end 7 of the cartridge body member 9. The cartridge body member 9 may then be fitted in a conventional bone cement gun 95 as illustrated in FIG. 8.

The bone cement may then be utilized in a normal fashion, or, it may be subjected to a prepressurization treatment, which has been found to be effective in certain instances. In this regard, it should be noted that in order to minimize the amount of air entrapped in the viscous mixture as air bubbles, the mixer is maximally evacuated of air. When the liquid monomer component of the bone cement is introduced into the mixing chamber, a small amount of the monomer will evaporate and equilibrate at the partial vapor pressure of the liquid monomer at that temperature. However, turbulence created by the mixer element during mixing, i.e. cavitation, will cause the monomer to boil. With higher vacuums, the mixture "cavitates" more easily. The monomer which boils under these conditions, and hence the bubbles of gaseous monomer formed in viscous mixture will only partially collapse when the vacuum is released, and may require a significant amount of time to collapse fully. Since most bone cements harden within about 8 to 15 minutes of mixing, the monomer bubbles may not have fully collapsed before hardening. Moreover, the heat of polymerization generated during the curing of the bone cement may actually cause the partially collapsed gaseous monomer bubbles to re-expand. Therefore, it has been found to be desirable to pressurize the bone cement shortly after release of the vacuum, but prior to use, hence the name "prepressurization" to accelerate the complete collapse of bubbles of gaseous monomer.

In order to effect the prepressurization treatment, the present invention provides a special pressure gauge cap 97 which may be fitted over the second open end 7 of the cartridge body member 9.

Figure 9A:
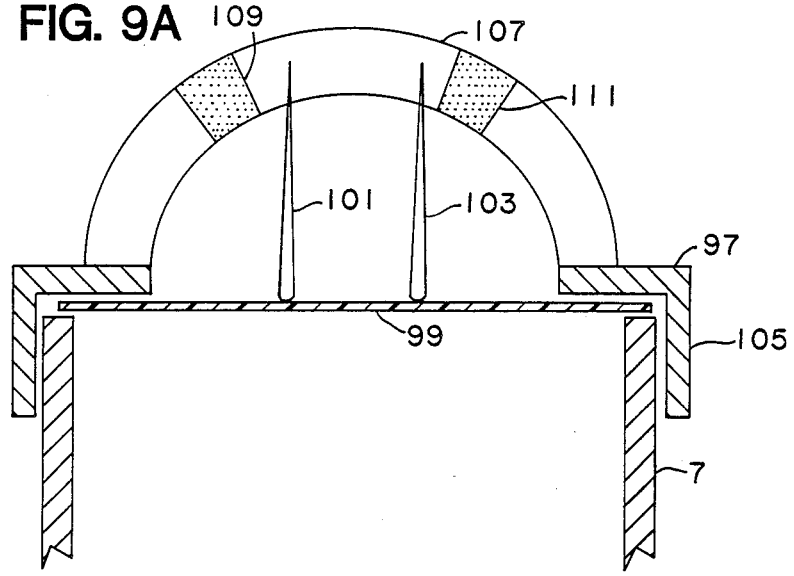
FIGS. 9A and 9B are schematic, partially sectioned illustrations of a pressure gauge for prepressurization of a bone cement cartridge.
Figure 9B:
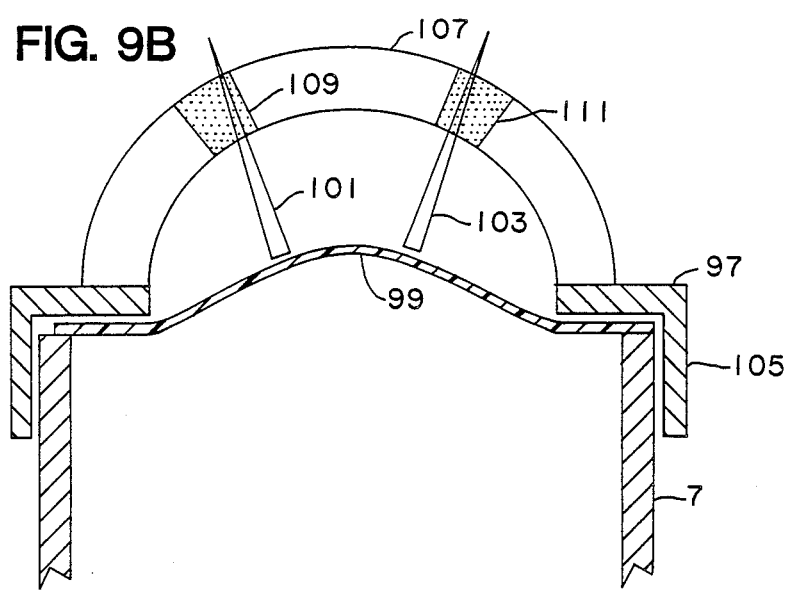

As illustrated in FIG. 9A, the cap 97 comprises a flexible membrane 99 having two protrusions 101, 103 extending substantially perpendicular therefrom; and a flange member 105 which may be screwed onto the end of the cartridge body member. The flange member incorporates an arcuate gauge element 107 having predetermined indicia 109 and 111 formed thereon. When the cartridge body member is mounted in the bone cement gun and subjected to pressure by movement of the plunger of the bone cement gun and concomitant movement of the piston member of the cartridge member, the increase in pressure causes distension of the membrane 99, as best seen in FIG. 9B. The distension of this membrane member causes the protrusions 101 and 103 to effectively bend outwardly away from one another and the degree of this bending is indicative of the internal pressure developed in the cartridge body member. By applying pressure until such time as the indicia 109 and 111 are substantially aligned with the protrusions 101 and 103, respectively, a predetermined pressure may be developed within the cartridge body member. After maintaining the pressure, e.g. 75 psig, for a predetermined period of time, the pressure may be released and the cap 97 removed.

Figure 17:
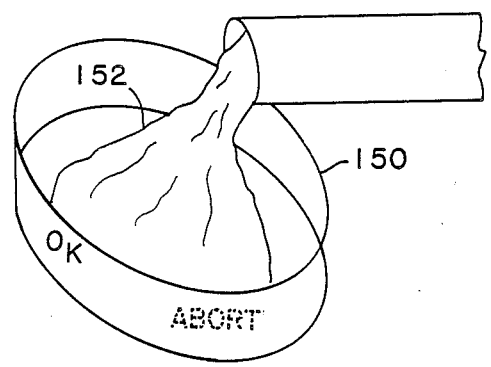
FIG. 17 is an illustration of a technique for testing for operability of the bone cement prepared according to the present invention.

In operation, a closure cap 120 may then be connected onto the open end 7 of the cartridge 9, as illustrated in FIG. 10, and a tip 121 is selected for the particular type of operation and is engaged with the front closure cap 120. (At this point, it is recommended that the first few cc's of the cement be wasted by squeezing the handle of the cement gun. This would allow the surgeon a feel of the flow (viscosity) of the cement from the nozzle of the cement gun prior to injecting it into the patient. If the cement is too stiff, the surgeon should abandon the use of the cement. Alternatively, the temperature of the cement is indicative of the degree of cure and the temperature may be used as the determinative factor in whether or not the cement should be utilized. In this regard, as shown in FIG. 17, a temperature sensitive tape, e.g., of the liquid crystal type, 150 may form the wall of a small container into which a few cc's of cement 152 is injected. Depending upon the type of cement utilized, the tape will have a temperature range in which further utilization of the cement is permissible ("OK") and above a certain temperature further utilization of the cement is not permissible ("ABORT"). One indicia, "OK" or "ABORT", only will be readily visible depending on the temperature of the cement. The engagement between the front closure cap 120 and the cartridge body member may be by means of a snap fit, an internal threading or an external threading. When a prosthesis is to be cemented to a plateau-type surface, holes 122 may be drilled into the bone surface to create a cavity into which bone cement 123 is to be injected, as shown in FIG. 10. An appropriate tip is selected which is configured to interfit with the opening of the bone cavity. The end of the tip is tapered inwardly to terminate in a portion having a diameter less than the diameter of the bone cavity. This allows the tapered portion of the tip to be inserted into the bone cavity and form a seal about the diameter of the bone cavity. Thus, the cement is injected into a closed space so that pressure can build up to force the cement to penetrate the trabeculae of the bone. Cement is also deposited over the remaining bone surface to which the prosthesis is to be attached.

In the case of a long tubular bone canal, some type of plug as shown in FIG. 11 must be lodged in the canal to create a closed space to prevent the extension of bone cement beyond the point where it is useful and to facilitate more complete filling and pressurization of the canal. Various means of plugging the canal have been advocated, including plugs made of natural bone, polyethylene or a bolus of doughy bone cement. Initially, a long straight tip 121b, which has a diameter less than the diameter of the canal to allow the tip to project into the bone canal, is used to deposit bone cement into the long bone canal. This tip 121b does not have a tapered end since the canal is initially just being filled up. Then, a tip such as the femoral canal pressurizer 140 and adapter 141, as shown in FIG. 12, is used to complete the filling of the canal and pressurize the contents of the cavity. The tapered pressurizer seals off the canal thereby enabling the pressure created upon injection of the cement to force the cement to penetrate the bone.

Throughout the specification, reference has been made to the air-impermeability of certain materials of construction which are utilized in the present invention. It should be noted that this terminology does not require perfect air-impermeability, however, it does require a degree of air-impermeability sufficient to prevent any significant loss of vacuum pressure through the material over the expected storage life of the vacuum packed materials, e.g. six months.

The mixing system disclosed in the present invention may be provided in the form of a kit comprising a double vacuum packed cartridge mixer filled with a first predetermined amount of a solid, powdery bone cement component, an ampoule containing a second predetermined amount of a liquid bone cement component, an injector for transfer of the liquid bone cement component to the cartridge mixer and a polyethylene ball for insertion in the ampoule prior to insertion in the injector so as to provide a positive sealing action to prevent air ingress into the cartridge mixer upon passage of the predetermined quantity of monomer thereto.

What is claimed is:

1. A two-component bone cement mixing system comprising:
   (A) a cartridge mixer means, having an interior volume containing a first predetermined quantity of a solid bone cement component under vacuum pressure, for mixing said first predetermined quantity of a solid bone cement component with a second predetermined quantity of a liquid bone cement component in the substantial absence of air to form a third predetermined quantity of a fluid two-component bone cement;

(B) container means for holding said second predetermined quantity of a liquid bone cement component, said container means comprising a hollow container body member having a longitudinal axis and a first end and a second end, said second end including a spout coaxial with said hollow body longitudinal axis and a removable closure member for said spout;

(C) fluid transfer means, operably connectable to said cartridge mixer means and said container means, for fluidically connecting said container means and said cartridge mixer means to transfer said second predetermined quantity of liquid bone cement component from said container means to said cartridge mixer means, said fluid transfer means comprising
a hollow injector body member having a longitudinal axis and a first open end and a second open end spaced apart on said longitudinal axis, said hollow injector body member slidingly receivable of said hollow container body member;
a cap member, disposed on said second open end of said hollow injector body member for closure thereof, said cap member including a fluid conduit for passage of a fluid through said cap member;
an elongate hollow tube, operably connectable to said cartridge mixer means and hermetically connectable to said fluid conduit;
support means, hermetically sealingly connecting said second end of said hollow injector body member and said cap member, for engagingly contacting said second end of said hollow container body member, said support means including a fluid passage fluidically connected to said fluid conduit and receivable of said spout of said hollow container body member;

(D) plug means, receivable within said container means, for automatically hermetically sealing said fluid transfer means against passage of a material therethrough upon completion of the transfer of said second predetermined quantity of a liquid bone cement component from said container means to said cartridge mixer means therethrough, said plug means comprising a float member having a specific gravity less than said liquid bone cement component, said float member sealingly receivable in said fluid passage in said support means.

2. The mixing system according to claim 1, wherein said cartridge mixer means containing said first predetermined quantity of a solid bone cement component under vacuum pressure is itself contained within a substantially air-impermeable container under vacuum pressure.

3. The mixing system according to claim 2, wherein said air-impermeable container is a plastic bag.

4. The mixing system according to claim 1, wherein said vacuum pressure in said cartridge mixer means is less than about 30 mm Hg.

5. The mixing system according to claim 1, wherein said cartridge mixer means comprises
cartridge means, receivable within a bone cement gun, for containing said third predetermined quantity of a fluid two-component bone cement, said cartridge means including piston means, operatively engageable by said bone cement gun and moveable within said cartridge means, for dispensing of said fluid two-component bone cement from said cartridge means;
mixer means, detachably connected to said cartridge means, for agitating the contents of said cartridge means, said mixer means including inlet port means, operably connectable to said fluid transfer means, for passage of said second predetermined quantity of a liquid bone cement component into said cartridge mixer means;
hermetic sealing means for sealing said connected cartridge means and mixer means against the ingress of air.

6. The mixing system according to claim 5, wherein said cartridge means comprises
a hollow cartridge body member having a longitudinal axis, and a first open end and a second open end spaced apart on said longitudinal axis;
a piston member, axially slidable within said hollow cartridge body member, disposed within said hollow cartridge body member proximate said first end of said cartridge body, to close said first end of said cartridge body.

7. The mixing system according to claim 6, wherein said mixer means comprises
a hollow mixer body member having a longitudinal axis, and a first open end and a second open end spaced apart on said longitudinal axis;
a cap member, disposed proximate said first end of said hollow mixer body, to close said first end of said hollow mixer body;
a self-sealing aperture, formed in said cap member, operably engageable by said fluid transfer means, for fluidic communication with said interior volume of said cartridge mixer means when engaged by said fluid transfer means and sealed closure of said interior volume when not engaged by said fluid transfer means;
a first aperture, formed in said cap member, receivable of a mixing element therethrough;
a movable mixing element, received in said first aperture and extending from said interior volume of said cartridge through said first aperture, movement of said mixing element causing agitation of the contents of said cartridge mixer means.

8. The mixing system according to claim 7, wherein said cartridge mixer means further comprises detachable connection means for detachably coaxially connecting said second end of said hollow cartridge body member to said second end of said hollow mixer body member.

9. The mixing system according to claim 8, wherein said detachable connection means comprises a first screw thread formed on an outer surface of said second end of said hollow cartridge body member and a second screw thread formed on an inner surface of said second end of said hollow mixer body member, said fist screw thread and said second screw thread being threadingly engageable of one another.

10. The mixing system according to claim 7, wherein said first aperture has an axis substantially parallel to said longitudinal axis of said hollow mixer body member and said movable mixing element has an axis coaxial with said axis of said first aperture.

11. The mixing system according to claim 10, wherein said mixer element is rotatably movable about said axis of said first aperture.

12. The mixing system according to claim 11, wherein said movable mixing element is axially slidable in said first aperture.

13. The mixing system of claim 1, wherein said hollow container body member, said spout and said removable closure member are made of glass.

14. The mixing system according to claim 1, wherein said float member is a polyethylene ball.

15. A cartridge mixer, having an interior volume, useful for the mixing of a first predetermined quantity of a solid bone cement component with a second predetermined quantity of a liquid bone cement component to form a third predetermined quantity of a fluid two-component bone cement, said cartridge mixer comprising
(A) cartridge means, receivable within a bone cement gun, for containing said third predetermined quantity of a fluid two-component bone cement, said cartridge means including piston means, operatively engageable by said bone cement gun and movable within said cartridge means, for dispensing of said fluid two-component bone cement from said cartridge means;
said cartridge means comprising
a hollow cartridge body member having a longitudinal axis, and a first open end and a second open end spaced apart on said longitudinal axis; said piston means comprising
a piston member, axially slidable within said hollow cartridge body member, disposed within said hollow cartridge body member proximate said first end of said cartridge body, to close said first end of said cartridge body;
(B) mixer means, detachably connected to said cartridge means, for agitating the contents of said cartridge means, said mixer means including inlet port means for passage of a second predetermined quantity of a liquid bone cement component into said cartridge mixer;
said mixer means comprising
a hollow mixer body member having a longitudinal axis, and a first open end and a second open end spaced apart on said longitudinal axis;
a cap member, disposed proximate said first end of said hollow mixer body, to close said first end of said hollow mixer body;
a self-sealing aperture, formed in said cap member, for fluidic communication with said interior volume of said cartridge mixer means;
a first aperture, formed in said cap meter, receivable of a mixing element therethrough;
a movable mixing element, received in said first aperture and extending from said interior volume of said cartridge through said first aperture, movement of said mixing element causing agitation of the contents of said mixer means;
(C) detachable connection means for detachably coaxially connecting said second end of said hollow cartridge body member to said second end of said hollow mixer body member; and
(D) hermetic sealing means for sealing said connected cartridge means and mixer means against the ingress of air.

16. The cartridge mixer according to claim 15, wherein said cartridge mixer contains a first predetermined quantity of a solid bone cement component under vacuum pressure.

17. The cartridge mixer according to claim 16, wherein said vacuum pressure is less than about 30 mm Hg.

18. The cartridge mixer according to claim 16, wherein said cartridge mixer is contained within a substantially air-impermeable container under vacuum pressure.

19. The cartridge mixer according to claim 18, wherein said air-impermeable container is a plastic bag.

20. The cartridge mixer according to claim 15, wherein said first aperture has an axis substantially parallel to said longitudinal axis of said hollow mixer body member and said movable mixing element has an axis coaxial with said axis of said first aperture.

21. The cartridge mixer according to claim 20, wherein said mixer element is rotatably movable about said axis of said first aperture.

22. The cartridge mixer according to claim 21, wherein said movable mixing element is axially slidable in said first aperture.

23. The cartridge mixer according to claim 22, wherein said mixer element comprises a plate member disposed substantially perpendicular to said axis of said first aperture, said plate element being axially movable within said hollow mixer body member, said plate element having a plurality of holes therethrough.

24. The cartridge mixer according to claim 23, wherein said hollow mixer body member is circular in cross-section, said plate member is circular in plan, said plurality of holes comprises a first plurality of pairs of holes, each of said pairs of holes comprising a hole with a first radius and a hole with a second radius, said first radius being larger than said second radius, each of said holes in a pair of holes being centered on a common diameter of said plate member and disposed on opposite sides of said plate center from one another.

25. The cartridge mixer according to claim 24, wherein each hole having said first radius is immediately adjacent and disposed between two holes having said second radius, in a circumferential direction.

26. The cartridge mixer according to claim 25, wherein said first plurality of pairs of holes comprises three pairs of holes and the common diameter of each pair of holes is offset 60° of arc from adjacent common diameters of holes.

27. A two-component bone cement kit comprising:
(A) a vacuum-packed cartridge mixer, defining an interior volume, containing a first predetermined quantity of a powdery bone cement component, said cartridge mixer comprising:
a cartridge member, receivable within a bone cement gun, comprising a hollow, air-impermeable cartridge body member having a longitudinal axis, and a first open end and a second open end spaced apart on said longitudinal axis.
an air-impermeable piston member, axially slidable within said hollow cartridge body, disposed within said cartridge body, proximate said first end of said cartridge body, to close said first end of said cartridge body,
releasable hermetic sealing means for releasably hermetically sealing said piston member to said cartridge body proximate said first end of said cartridge body,
a mixer member comprising a hollow, air-impermeable mixer body having a longitudinal axis, and a first open end and a second open end spaced apart on said longitudinal axis, releasable connection means for releasably coaxially hermetically sealing connecting said second end of said cartridge body member to said second end of said mixer body for fluidic communication between said cartridge body member and said mixer body, and cap means for hermetically sealing said first end of said mixer body, said cap means including self-sealing aperture means, pierceable by a hollow needle, for fluidic communication with said interior volume of said cartridge mixer through said hollow needle when pierced by said hollow needle and hermetically sealed closure of said interior volume when said hollow needle is withdrawn, and mixing means for agitating a material contained within said interior volume of said cartridge mixer;

(B) an ampoule, defining an interior volume, containing a second predetermined quantity of a liquid bone cement component, said ampoule comprising a liquid bone cement component impermeable body member having a longitudinal axis, spout means, having a predetermined diameter, for fluid communication with said interior volume of said ampoule and removable closure means for hermetically sealing said spout means;

(C) an injector comprising a hollow injector body member having a longitudinal axis and a first open end and a second open end spaced apart on said longitudinal axis, said hollow injector body member slidingly, coaxially receivable of said ampoule, a cap member, disposed on said second open end of said hollow injector body for closure thereof, said cap member including a fluid conduit, coaxial with said hollow body, for passage of a fluid through said cap member, hollow needle means, pierceable of said self-sealing aperture means, hermetically connectable to said fluid conduit, for passage of fluid into said interior volume of said cartridge mixer, resilient support means, hermetically sealingly connecting said second end of said hollow injector body and said cap member, for engagingly contacting said ampoule, said resilient support means including a fluid passage tapering toward and fluidically connected to said fluid conduit, said fluid passage coaxial with said hollow injector body and receivable of said ampoule spout means; and (D) float means, having a specific gravity less than said liquid bone cement component, for hermetically sealingly closing said fluid passage in said resilient support means.

28. The bone cement kit according to claim 27, wherein said float means comprises a polyethylene ball.

29. A method of preparing a bone cement comprising:

providing a cartridge mixer means, having an interior volume containing a first predetermined quantity of a solid bone cement component under vacuum pressure, for mixing said first predetermined quantity of a solid bone cement component with a second predetermined quantity of a liquid bone cement component in the substantial absence of air to form a third predetermined quantity of a fluid two-component bone cement;

providing container means, containing said second predetermined quantity of a liquid bone cement component, for holding a liquid bone cement component;

cooling said cartridge mixer means containing said solid bone cement component and said container means containing said liquid bone cement component to a temperature less than 20° C.;

then admixing said liquid bone cement component and said solid bone cement component in said cartridge mixer means while maintaining said vacuum pressure in said cartridge mixer means.

30. The method according to claim 29, wherein said cooling is to a temperature of less than 15° C.

31. The method according to claim 29, wherein said cooling is to a temperature of about 12° C.

32. The method according to claim 29, wherein said vacuum pressure is less than about 30 mm Hg.

33. A two-component bone cement mixing system comprising:

(A) a cartridge mixer means, having an interior volume containing a first predetermined quantity of a solid bone cement component under vacuum pressure, for mixing said first predetermined quantity of a solid bone cement component with a second predetermined quantity of a liquid bone cement component in the substantially absence of air to form a third predetermined quantity of a fluid two-component bone cement;

said cartridge mixer means comprising (a) cartridge means, receivable within a bone cement gun, for containing said third predetermined quantity of a fluid two-component bone cement, said cartridge means including piston means, operatively engageable by said bone cement gun and moveable within said cartridge means, for dispensing of said fluid two-component bone cement from said cartridge means;

said cartridge means comprising a hollow cartridge body member having a longitudinal axis, and a first open end and a second open end spaced apart on said longitudinal axis; said piston means comprising a piston member, axially slidable within said hollow cartridge body member, disposed within said hollow cartridge body member proximate said first end of said cartridge body, to close said first end of said cartridge body;

(b) mixer means, detachably connected to said cartridge means, for agitating the contents of said cartridge means, said mixer means including inlet port means, operably connectable to said fluid transfer means, for passage of said second predetermined quantity of a liquid bone cement component into said cartridge mixer means;

said mixer means comprising a hollow mixer body member having a longitudinal axis, and a first open end and a second open end spaced apart on said longitudinal axis;

a cap member, disposed proximate said first end of said hollow mixer body, to close said first end of said hollow mixer body;

a self-sealing aperture, formed in said cap member, operably engageable by said fluid transfer means, for fluidic communication with said interior volume of said cartridge mixer means when engaged by said fluid transfer means and sealed closure of said interior volume when not engaged by said fluid transfer means;

a first aperture, formed in said cap member, receivable of a mixing element therethrough;

a movable mixing element, received in said first aperture and extending from said interior volume of said cartridge through said first aperture, movement of said mixing element causing agitation of the contents of said cartridge mixer means;

(c) detachable connection means for detachably coaxially connecting said second end of said hollow cartridge body member to said second end of said hollow mixer body member;

(d) hermetic sealing means for sealing said connected cartridge means and mixer means against the ingress of air;

(B) container means for holding said second predetermined quantity of a liquid bone cement component;

(C) fluid transfer means, operably connectable to said cartridge mixer means and said container means, for fluidically connecting said container means and said cartridge mixer means to transfer said second predetermined quantity of a liquid bone cement component from said container means to said cartridge mixer means;

(D) plug means, receivable within said container means, for automatically hermetically sealing said fluid transfer means against passage of a material therethrough upon completion of the transfer of said second predetermined quantity of a liquid bone cement component from said container means to said cartridge mixer means therethrough.

34. A cartridge mixer, having an interior volume, useful for the mixing of a first predetermined quantity of a solid bone cement component with a second predetermined quantity of a liquid bone cement component to form a third predetermined quantity of a fluid two-component bone cement, said cartridge mixer comprising (A) cartridge means, receivable within a bone cement gun, for containing said third predetermined quantity of a fluid two-component bone cement, said cartridge means including piston means, operatively engageable by said bone cement gun and movable within said cartridge means, for dispensing of said fluid two-component bone cement from said cartridge means; said cartridge means comprising a hollow cartridge body member having a longitudinal axis, and a first open end and a second open end spaced apart on said longitudinal axis;

said piston means comprising a piston member, axially slidable within said hollow cartridge body member, disposed within said hollow cartridge body member proximate said first end of said cartridge body, to close said first end of said cartridge body;

(B) mixer means, detachably connected to said cartridge mans, for agitating the contents of said cartridge means, said mixer means including inlet port means for passage of a second predetermined quantity of a liquid bone cement component into said cartridge mixer;

said mixer means comprising a hollow mixer body member having a longitudinal axis, and a first open end and a second open end spaced apart on said longitudinal axis;

a cap member, disposed proximate said first end of said hollow mixer body, to close said first end of said hollow mixer body;

a self-sealing aperture, formed in said cap member, for fluidic communication with said interior volume of said cartridge mixer means;

a first aperture, formed in said cap member, receivable of a mixing element therethrough;

a movable mixing element, received in said first aperture and extending from said interior volume of said cartridge through said first aperture, movement of said mixing element causing agitation of the contents of said cartridge mixer means;

wherein said first aperture has an axis substantially parallel to said longitudinal axis of said hollow mixer body member and said movable mixing element has an axis coaxial with said axis of said first aperture, said mixer element is rotatably movable about said axis of said first aperture, said movable mixing element is axially slidable in said first aperture, and said mixer element comprises a plate member disposed substantially perpendicular to said axis of said first aperture, said plate element being axially movable within said hollow mixer body member, said plate element having a plurality of holes therethrough;

(C) hermetic sealing means for sealing said connected cartridge means and mixer means against the ingress of air.

35. The cartridge mixer according to claim 34, wherein said hollow mixer body member is circular in cross-section, said plate member is circular in plan, said plurality of holes comprises a first plurality of pairs of holes, each of said pairs of holes comprising a hole with a first radius and a hole with a second radius, said first radius being larger than said second radius, each of said holes in a pair of holes being centered on a common diameter of said plate member and disposed on opposite sides of said plate center from one another.

36. The cartridge mixer according to claim 35, wherein each hole having said first radius is immediately adjacent and disposed between two holes having said second radius, in a circumferential direction.

37. The cartridge mixer according to claim 36, wherein said first plurality of pairs of holes comprises three pairs of holes and the common diameter of each pair of holes is offset 60° of arc from adjacent common diameters of holes.

* * * * *